(12) United States Patent
Astier et al.

(10) Patent No.: US 9,097,698 B2
(45) Date of Patent: Aug. 4, 2015

(54) NANOGAP DEVICE WITH CAPPED NANOWIRE STRUCTURES

(71) Applicant: International Business Machines Corporation, Armonk, NY (US)

(72) Inventors: Yann A. N. Astier, White Plains, NY (US); Jingwei Bai, San Diego, CA (US); Satyavolu S. Papa Rao, Poughkeepsie, NY (US); Kathleen B. Reuter, Montrose, NY (US); Joshua T. Smith, Croton on Hudson, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 14/608,781

(22) Filed: Jan. 29, 2015

(65) Prior Publication Data

US 2015/0137069 A1    May 21, 2015

Related U.S. Application Data

(60) Division of application No. 14/041,922, filed on Sep. 30, 2013, which is a continuation-in-part of application No. 13/945,295, filed on Jul. 18, 2013, which is a continuation of application No. 13/921,383, filed on Jun. 19, 2013.

(51) Int. Cl.
*G01N 33/487* (2006.01)
*H01L 29/06* (2006.01)
*H01L 29/41* (2006.01)

(52) U.S. Cl.
CPC ...... *G01N 33/48721* (2013.01); *H01L 29/0669* (2013.01); *H01L 29/413* (2013.01)

(58) Field of Classification Search
None
See application file for complete search history.

(56) References Cited

U.S. PATENT DOCUMENTS

| 4,576,829 A | 3/1986 | Kaganowicz et al. |
| 4,692,992 A | 9/1987 | Hsu |
| 5,671,086 A | 9/1997 | Parvin et al. |

(Continued)

FOREIGN PATENT DOCUMENTS

| CN | 101203740 A | 6/2008 |
| CN | 101385126 A | 3/2009 |

(Continued)

OTHER PUBLICATIONS

Harrer et. al., Electrochemical protection of thin film electrodes in solid state nanopores, Nanotechnology 22 (2011) 275304 (6pp), publication date: May 20, 2011.*

(Continued)

*Primary Examiner* — Andres Munoz
(74) *Attorney, Agent, or Firm* — Cantor Colburn LLP; Vazken Alexanian

(57) ABSTRACT

An anti-retraction capping material is formed on a surface of a nanowire that is located upon a dielectric membrane. A gap is then formed into the anti-retraction capping material and nanowire forming first and second capped nanowire structures of a nanodevice. The nanodevice can be used for recognition tunneling measurements including, for example DNA sequencing. The anti-retraction capping material serves as a mobility barrier to pin, i.e., confine, a nanowire portion of each of the first and second capped nanowire structures in place, allowing long-term structural stability. In some embodiments, interelectrode leakage through solution during recognition tunneling measurements can be minimized.

10 Claims, 6 Drawing Sheets

(56) References Cited

U.S. PATENT DOCUMENTS

| | | |
|---|---|---|
| 6,180,490 B1 | 1/2001 | Vassiliev et al. |
| 6,217,872 B1 | 4/2001 | Okayama et al. |
| 6,413,792 B1 | 7/2002 | Sauer et al. |
| 6,582,926 B1 | 6/2003 | Chilkoti |
| 6,621,191 B1 | 9/2003 | Nomura et al. |
| 6,627,067 B1 | 9/2003 | Branton et al. |
| 6,727,174 B1 | 4/2004 | Kotecki et al. |
| 6,777,260 B1 | 8/2004 | Chen |
| 6,783,643 B2 | 8/2004 | Golovchenko et al. |
| 6,962,849 B1 | 11/2005 | Kamal et al. |
| 7,282,130 B2 | 10/2007 | Flory |
| 7,347,921 B2 | 3/2008 | Barth et al. |
| 7,351,648 B2 | 4/2008 | Furukawa et al. |
| 7,468,271 B2 | 12/2008 | Golovchenko et al. |
| 7,540,717 B2 | 6/2009 | Sheng et al. |
| 7,553,730 B2 | 6/2009 | Barth et al. |
| 7,560,141 B1 | 7/2009 | Kim et al. |
| 7,582,490 B2 | 9/2009 | Golovchenko et al. |
| 7,846,738 B2 | 12/2010 | Golovchenko et al. |
| 2004/0229386 A1 | 11/2004 | Golovchenko et al. |
| 2005/0019784 A1 | 1/2005 | Su et al. |
| 2005/0026238 A1 | 2/2005 | Berndt |
| 2005/0101100 A1 | 5/2005 | Kretchmer et al. |
| 2005/0110990 A1 | 5/2005 | Koo et al. |
| 2005/0158763 A1 | 7/2005 | Ivanisevic et al. |
| 2005/0202446 A1 | 9/2005 | Yang et al. |
| 2006/0105553 A1 | 5/2006 | Wellhausen et al. |
| 2006/0154399 A1 | 7/2006 | Sauer et al. |
| 2006/0154400 A1 | 7/2006 | Choi et al. |
| 2006/0169588 A1 | 8/2006 | Jacobson et al. |
| 2006/0180469 A1 | 8/2006 | Han et al. |
| 2006/0246497 A1 | 11/2006 | Huang et al. |
| 2006/0275778 A1 | 12/2006 | Wu et al. |
| 2007/0020146 A1 | 1/2007 | Young et al. |
| 2007/0042366 A1 | 2/2007 | Ling |
| 2007/0048745 A1 | 3/2007 | Joyce et al. |
| 2007/0138132 A1 | 6/2007 | Barth |
| 2007/0187694 A1 | 8/2007 | Pfeiffer |
| 2007/0190542 A1 | 8/2007 | Ling et al. |
| 2008/0003571 A1 | 1/2008 | McKernan et al. |
| 2008/0032290 A1 | 2/2008 | Young |
| 2008/0102504 A1 | 5/2008 | Akeson et al. |
| 2008/0105539 A1 | 5/2008 | Lyding et al. |
| 2008/0119366 A1 | 5/2008 | Sauer et al. |
| 2008/0187915 A1 | 8/2008 | Polonsky et al. |
| 2008/0257859 A1 | 10/2008 | Golovchenko et al. |
| 2009/0136958 A1 | 5/2009 | Gershow et al. |
| 2009/0188794 A1 | 7/2009 | Simon et al. |
| 2009/0221443 A1 | 9/2009 | Heller et al. |
| 2009/0222216 A1 | 9/2009 | Hibbs et al. |
| 2009/0295372 A1 | 12/2009 | Krstic et al. |
| 2010/0009134 A1 | 1/2010 | Drndic et al. |
| 2010/0025249 A1 | 2/2010 | Polonsky et al. |
| 2010/0032302 A1 | 2/2010 | Holtermann et al. |
| 2010/0084276 A1 | 4/2010 | Lindsay |
| 2010/0142259 A1 | 6/2010 | Drndic et al. |
| 2010/0144535 A1 | 6/2010 | Strachan et al. |
| 2010/0327255 A1 | 12/2010 | Peng et al. |
| 2010/0327847 A1* | 12/2010 | Leiber et al. ............. 324/71.1 |
| 2010/0331194 A1 | 12/2010 | Turner et al. |
| 2011/0052813 A1 | 3/2011 | Ho et al. |
| 2011/0085759 A1 | 4/2011 | Lee et al. |
| 2011/0120868 A1 | 5/2011 | Lindsay et al. |
| 2011/0220574 A1 | 9/2011 | Bakajin et al. |
| 2011/0236984 A1 | 9/2011 | Sun et al. |
| 2011/0268647 A1 | 11/2011 | Ivanovici et al. |
| 2011/0279125 A1 | 11/2011 | Bedell et al. |
| 2012/0146162 A1 | 6/2012 | Cho et al. |
| 2012/0193235 A1 | 8/2012 | Afzali-Ardakani et al. |
| 2012/0193236 A1 | 8/2012 | Peng et al. |
| 2012/0193237 A1 | 8/2012 | Afzali-Ardakani et al. |
| 2012/0288948 A1 | 11/2012 | Lindsay et al. |
| 2013/0037410 A1 | 2/2013 | Xu et al. |
| 2013/0203050 A1 | 8/2013 | Huber et al. |
| 2013/0265031 A1 | 10/2013 | Shim et al. |

FOREIGN PATENT DOCUMENTS

| | | |
|---|---|---|
| EP | 0261592 A1 | 9/1987 |
| EP | 1441213 A1 | 7/2004 |
| EP | 1486775 | 12/2004 |
| WO | WO0181908 A | 11/2001 |
| WO | WO2006122317 A2 | 11/2006 |
| WO | WO2007084163 A | 7/2007 |
| WO | WO2008051308 A2 | 5/2008 |
| WO | WO2008132643 A1 | 11/2008 |
| WO | WO2009020682 A2 | 2/2009 |
| WO | WO2009032756 A2 | 3/2009 |
| WO | WO2009117522 A2 | 9/2009 |

OTHER PUBLICATIONS

A. P. Ivanov et al., "DNA tunneling detector embedded in a nanopore," Nano Letters, vol. 11, No. 1, Jan. 12, 2011, pp. 279-285.

D. Branton et al., "The Potential and Challenges of Nanopore Sequencing," Nat. Biotech., vol. 26 (10), pp. 1146-1153 Author Manuscript (Oct. 2008); 17 pages.

Heng, Jiunn B. et al., "Sizing DNA Using a Nanometer-Diameter Pore", Biophysical Journal, vol. 87, Oct. 2004, pp. 2905-2911.

International Search Report—PCT; Notification of Transmittal of The International Search Report and The Written Opinion of the International Searching Authority, or the Declaration; Apr. 5, 2011; International application No. PCT/US1123872; pp. 1-8.

J. Prasongkit et al., "Transverse conductance of DNA necleotides in a graphene nanogap from first principles," arXiv:1012.1669v2 [physics.ins-det], [v1] Dec. 8, 2010, [v2] Jan. 14, 2011, Nano Lett., vol. 11, No. 5, 2011, pp. 1941-1945.

Kasianowicz, John J., et al., "Characterization of individual polynucleotide molecules using a membrane channel", Proc. Natl. Acad. Sci. USA, vol. 93, Nov. 1996, pp. 13770-13773.

Lagerqvist, Johan et al., "Fast DNA Sequencing via Transverse Electronic Transport", Nano Lett., vol. 6, No. 4, Received Jan. 17, 2006; revised Manuscript Received Mar. 1, 2006, pp. 779-782.

M. Fedurco, A. Romieu, S. Williams, I. Lawrence, G. Turcatti, "BTA, a Novel Reagent for DNA Attachment on Glass and Efficient Generation of Solid-phase Amplified DNA Colonies," Nucleic Acids Res. vol. 34, pp. e22 (2006).

M. Margulies et al., "Genome Sequencing in Mircrofabricated Highdensity Pico-litre Reactors," Nature, vol. 437, pp. 376-380 (2005).

Notification of Transmittal of The International Search Report and The Written Opinion of the International Searching Authority, or the Declaration; Mail date: Oct. 30, 2014; Int'l App. No. PCT/US14/37235; Int'l Filing Date: May 8, 2014; 16 pages.

Polonsky et al., "Nanopore in metal-dielectric sandwich for DNA position control," Applied Physics Letters 91, 153103 (2007), pp. 1-3.

S. Chang et al., "Electronic signatures of all four DNA nucleosides in a tunneling gap," Nano Letters, vol. 10, No. 3, 2010, pp. 1070-1075.

S. Chang et al., "Chemical recognition and binding kinetics in a functionalized tunnel junction," Nanotechnology, vol. 23, No. 23, 2012, 235101, 14 pages.

S. Roy et al., "Direct Electrical Measurements on Single-Molecule Genomic DNA Using Single-Walled Carbon Nanotubes," Nano Letters, vol. 8, No. 1, 2008, pp. 26-30.

S. Vassanelli, P. Fromherz, "Transistor Probes Local Potassium Conductances in the Adhesion Region of Cultured Rat Hippocampal Neurons," The Journal of Neuroscience, Aug. 15, 1999, 19(16):6767-6773, Department of Membrane and Neurophysics, Max-Planck-I.

Soni, Gautam V. et al., "Progress toward Ultrafast DNA Sequencing Using Solid-State Nanopores", Clinical Chemistry, vol. 53, No. 11, (2007), pp. 1-6.

T. D. Harris et al., "Single-molecule DNA Sequencing of a Viral Genome," Science, vol. 320, pp. 106-109 (2008).

T. Kiefer et al., "A single nanotrench in a palladium microwire for hydrogen detection," Nanotechnology, vol. 19, No. 12, 2008, 125502, 9 pages.

T. Nagase et al., "Maskless fabrication of nanogap electrodes by using Ga-focused ion beam etching." Journal of Micro/Nanolithography, MEMS, and MOEMS, vol. 5, No. 1, 2006, 011006, 6 pages.

(56) References Cited

OTHER PUBLICATIONS

U.S. Appl. No. 12/820,543, filed Jun. 22, 2010; Title: Forming an Electrode Having Reduced Corrosion and Water Decomposition on Surface Using an Organic Protective Layer; Harrer et al.
U.S. Appl. No. 13/248,176; Title: Selective Placement of Carbon Nanotubes via Coulombic Attraction of Oppositely Charged Carbon Nonotubes and Self-Assembled Monolayers; Filing Date: Sep. 29, 2011; First Named Inventor: Ali Afzali-Ardak.
A. Bergvall et al., "Graphene nanogap for gate-tunable quantum-coherent single-molecule electronics," Phys. Rev. B, vol. 84, No. 15, 2011, 155451, 7 pages.
A. J. Storm et al., "Fabrication of solid-state nanopores with single-nanometre precision," Nature Materials, vol. 2, Aug. 2003, pp. 537-540.
A. K. Geim and K. S. Novoselov, "The Rise of Graphene," Nature Materials 6, 183 (2007), 9 pages.
A. Sidorenko et al., "Controlled Switching of the Wetting Behavior of Bioimetic Surfaces with Hydrogel-Supported Nanostructures," J. Mater. Chem., vol. 18, 2008, pp. 3841-3846.
Akeson, Mark, et al., "Microsecond Time-Scale Discrimination Among Polycytidylic Acid, Polyadenylic Acid, and Polyuridylic Acid as Homopolymers or as Segments Within Single RNA Molecules," Biophysical Journal, vol. 77, Dec. 1999, pp. 3227-3233.
Amit Meller et al., "Rapid nanopore discrimination between single polynucleotide molecules," PNAS, Feb. 1, 2000, vol. 97, No. 3, pp. 1079-1084.
B. Luan et al., "DNA-translocation through a solid state nanopore coated with a self-assembled monolayer," Bull. Am. Phys. Soc., APS March Meeting 2011, vol. 56, No. 1, Abstract V43.00002, Mar. 24, 2011, 1 page.
B. Luan et al., "Tribological Effects on DNA Translocation in a Nanochannel Coated with a Self-Assembled Monolayer," J. Phys. Chem. B, vol. 114, 2010, pp. 17172-17176.
B. Luan, A. Aksimentiev, "Control and Reversal of the Electrophoretic Force on DNA in a Charged Nanopore," J. Phys. Condens. Matter, vol. 22, pp. 454123 (2010).
B. Luan, H. Peng, S. Polonsky, S. Rossnagel, G. Stolovitzky, and G. Martyna, "Base-by-base Ratcheting of Single-stranded DNA Through a Solid-state Nanopore," Phys. Rev. Lett., vol. 104 (23) pp. 238103-1-238103-4 (2010).
Bae, S. et al., "Roll-to-Roll Production of 30-inch Graphene Films for Transparent Electrodes," Nature Nanotechnology, Published online: Jun. 20, 2010, 5 pages.
D. W. Hess, "Plasma-assisted oxidation, anodization, and nitridation of silicon," IBM J. Res. Develop. vol. 43. No. 1/2, Jan./Mar. 1999, pp. 127-145.
Douville, et al., "DNA Linearization Through Confinement in Nanofluidic Channels, Anal Bioanal Chem.", Aug. 2008; vol. 391; No. 7; pp. 2395-2409; Abstract; p. 2402, col. 2; para 5; p. 2406; col. 2; para 2; p. 2407; Fig. 5b.
F. Patolsky, et al., "Electrical detection of single viruses," PNAS; Sep. 28, 2004; vol. 101, No. 39; pp. 14017-14022.
F. S. Collins, M. Morgan, A. Patrinos, "The Human Genome Project—Lessons From Large-scale Biology," Science, vol. 300, pp. 286-290 (2003).
F. Sanger, S. Nicklen, A. R. Coulson, "DNA sequencing with chain termination inhibitors," Proc. Natl. Acad. Sci USA., vol. 74 (12), pp. 5463-5467 (1977).
G. Sigalov, et al., "Detection of DNA Sequences Using an Alternating Electric Field in a Nanopore Capacitor," Nano Letters 2008, vol. 8, No. 1; pp. 56-63.

G. Tizazu et al., "Photopatterning, Etching, and Derivatization of Self-Assembled Monolayers of Phosphonic Acids on the Native Oxide of Titanium," Langmuir, vol. 25, 2009, pp. 10746-10753.
G. Turcatti, A. Romieu, M. Fedurco, A. P. Tairi, "A New Class of Cleavable Fluorescent Nucleotides: Synthesis and Optimization as Reversible Terminators for DNA Sequencing by Synthesis," Nucleic Acids Res., vol. 36, pp. e25 (2008).
G. Wang et al., "Photon Gated Transport at the Glass Nanopore Electrode," J. Am. Chem. Soc., vol. 128, 2006, pp. 13553-13558.
Gracheva, Maria E. et al., "Simulation of the electric response of DNA translocation through a semiconductor nanopore—capacitor", Institute of Physics Publishing, Nanotechnology, vol. 17 (2006), pp. 622-633.
H. Stranneheim, et al., "Stepping Stones in DNA Sequencing," Biotechnical Journal (2012) 7 (9) pp. 1063-1073.
H.W.C. Postma, "Rapid Sequencing of Individual DNA Molecules in Graphene Nanogaps," Nano Letters, vol. 10, No. 2, Jan. 4, 2010, pp. 420-425.
He, et al., "Identification of DNA Basepairing via Tunnel-Current Decay," Nano Letters 2007; vol. 7, No. 12; pp. 3854-3858.
I. Braslavsky, B. Hebert, E. Kartalov, S. R. Quake, "Sequence Information Can Be Obtained from Single DNA Molecules," Proc. Natl. Acad. Sci. USA, vol. 100, pp. 3960-3964 (2003).
J. Hass, W.A. De Heer and E.H. Conrad, "The Growth and Morphology of Epitaxial Multilayer Graphene," Journal of Physics: Condensed Matter 20, 323202 (2008), 28 pages.
J. Li et al., "Ion-beam sculpting at nanometre length scales," Nature, vol. 412, 2001, pp. 166-169.
J. Shedure et al., "Accurate Multiplex Polony Sequencing of an Evolved Bacterial Genome," Science, vol. 309, pp. 1728-1732 (2005).
K. McKernan, A. Blanchard, L. Kotler, G. Costa, "Reagents, Methods, and Libraries for Bead-based Sequencing," US Patent Application 20080003571 (2006).
K.S. Kim, Y. Zhao, H. Jang, S.Y. Lee, J. M. Kim, K. S. Kim, J. H. Ahn, P. Kim, J. Y. Choi, B. H. Hong, "Large-Scale Pattern Growth of Graphene Films for Stretchable Transparent Electrodes," Nature 457, 706-710 (2009).
M. J. Kim et al., "Rapid Fabrication of Uniformly Sized Nanopores and Nanopore Arrays for Parallel DNA Analysis," Adv. Mater. 2006, 18, pp. 3149-3153.
M. Tsutsui et al., "Identifying single nucleotides by tunnelling current," Nature Nanotechnology, vol. 5, 2010, pp. 286-290.
Meller A., Nivon L., Brandin E., Golovchenko J. and Branton D., "Rapid Nanopore Discrimination Between Signle Polynucleotide Molecules," Proc. Natl Acad. Sci. USA 97 1079-84 (2000).
Novoselov K S et al, "Electric Field Effect in Atomically Thin Carbon Films" Oct. 22, 2004 vol. 306 Science; pp. 666-669.
S. Harrer et al. "Electrochemical Characterization of Thin Film Electrodes Towards Developing a DNA-Transistor," Langmuir, vol. 26 (24), pp. 19191-19198 (2010).
S. Harrer et al., "Electrochemical Protection of Thin Film Electrodes in Solid State Nanopore," Nanotechnology, vol. 22, 2011, 275304, 6 pages.
Schedin F et al: "Detection of Individual Gas Molecules Absorbed on Graphene" Nature Materials Nature Publishing Group, UK, vol. 6, No. 9, Sep. 2007, pp. 652-655, XP002506772, ISSN: 1476-1122, the whole document.
Stern, E., et al., "Label-free immunodetection with CMOS-compatible semiconducting nanowires," Nature Letters, vol. 455 Feb. 1, 2007; 2007 Nature Publishing Group; pp. 519-522.

* cited by examiner

NANOGAP DEVICE WITH CAPPED NANOWIRE STRUCTURES

This application is a divisional of U.S. Ser. No. 14/041,922, filed Sep. 30, 2013, which is a continuation-in-part application of U.S. Ser. No. 13/945,295, filed Jul. 18, 2013, which is a continuation application of U.S. Ser. No. 13/921,383, filed Jun. 19, 2013, the entire contents of all applications are incorporated herein by reference.

BACKGROUND

The present application relates to a nanodevice, and more particularly, to a sub-3 nm nanogap device containing capped nanowire structures located on a surface of a dielectric membrane.

Nanopore sequencing is a method for determining the order in which nucleotides occur on a strand of deoxyribonucleic acid (DNA). A nanopore (also referred to as pore, nanochannel, hole, etc.) can be a small hole in the order of several nanometers in internal diameter. The theory behind nanopore sequencing is about what occurs when the nanopore is submerged in a conducting fluid and an electric potential (voltage) is applied across the nanopore. Under these conditions, a slight electric current due to conduction of ions through the nanopore can be measured, and the amount of current is very sensitive to the size and shape of the nanopore. If single bases or strands of DNA pass (or part of the DNA molecule passes) through the nanopore, this can create a change in the magnitude of the current through the nanopore. Other electrical or optical sensors can also be positioned around the nanopore so that DNA bases can be differentiated while the DNA passes through the nanopore.

The DNA can be driven through the nanopore by using various methods, so that the DNA might eventually pass through the nanopore. The scale of the nanopore can have the effect that the DNA may be forced through the hole as a long string, one base at a time, like a thread through the eye of a needle. Recently, there has been growing interest in applying nanopores as sensors for rapid analysis of biomolecules such as deoxyribonucleic acid (DNA), ribonucleic acid (RNA), protein, etc. Special emphasis has been given to applications of nanopores for DNA sequencing, as this technology holds the promise to reduce the cost of sequencing below $1000/human genome.

SUMMARY

An anti-retraction capping material is formed on a surface of a nanowire that is located upon a dielectric membrane. A gap is then formed into the anti-retraction capping material and nanowire forming first and second capped nanowire structures of a nanodevice. The nanodevice can be used for recognition tunneling measurements including, for example DNA sequencing. The anti-retraction capping material serves as a mobility barrier to pin, i.e., confine, a nanowire portion of each of the first and second capped nanowire structures in place, allowing long-term structural stability. In some embodiments, interelectrode leakage through solution during recognition tunneling measurements can be minimized.

In one aspect of the present application, a method of forming a nanogap device is provided. In one embodiment of the present application, the method includes providing a dielectric membrane on a front-side surface of a semiconductor substrate. A nanowire is then formed on a surface of the dielectric membrane. An anti-retraction capping material is deposited on an upper surface of the nanowire. Next, the anti-retraction capping material and the nanowire are cut to provide a first capped nanowire structure and a second capped nanowire structure. The first capped nanowire structure and the second capped nanowire structure are separated by a nanogap of less than 3 nanometers.

In another aspect of the present application, a nanogap device is provided. In one embodiment of the present application, the nanogap device includes a dielectric membrane located on a front-side surface of a semiconductor substrate. A first capped nanowire structure is located on a first portion of the dielectric membrane, and a second capped nanowire structure is located on a second portion of the dielectric membrane. In accordance with the present application, the first capped nanowire structure and the second capped nanowire structure are separated by a nanogap of less than 3 nanometers.

DETAILED DESCRIPTION

Figure 1:
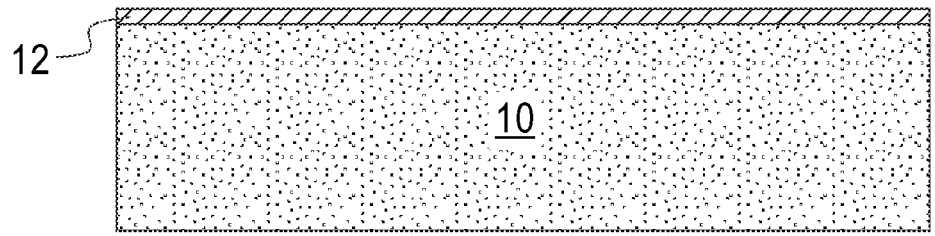
FIG. 1 is a cross sectional view of a first exemplary structure including, from bottom to top, a semiconductor substrate and a dielectric membrane in accordance with an embodiment of the present application.

The present application will now be described in greater detail by referring to the following discussion and drawings that accompany the present application. It is noted that the drawings of the present application are provided for illustrative purposes only and, as such, the drawings are not drawn to scale. It is also noted that like and corresponding elements are referred to by like reference numerals.

In the following description, numerous specific details are set forth, such as particular structures, components, materials, dimensions, processing steps and techniques, in order to provide an understanding of the various embodiments of the present application. However, it will be appreciated by one of ordinary skill in the art that the various embodiments of the present application may be practiced without these specific details. In other instances, well-known structures or processing steps have not been described in detail in order to avoid obscuring the present application.

The ability to rapidly sequence individual strands of DNA would enable a broad range of applications including, for example, discovering and understanding protein structures or detecting predispositions to diseases such as cancer. Single-based tunneling recognition is one approach that can be used to enable high-through-put, low-cost DNA sequencing because it reduces the amount of preparation that a target DNA requires to ready it from sequencing, i.e., copying is not necessary. While single-base recognition has been demonstrated using a scanning tunneling microscope (STM) approach, the failure to reproduce this capability on a technologically relevant platform has stemmed, in large part, from fabrication challenges that appear in structures with dimensions in the few nanometer range. Specifically, DNA sequencing by tunneling recognition on a manufacturable platform requires that the signature tunneling current from each individual base be read by a tunneling gap electrode which must be less than 3 nm wide and able to maintain a fixed gap width.

As an electrode material, palladium and gold are considered to be ideal candidates for DNA sensing because such conductive metals are excellent linkers for chemicals that are used to functionalize the electrodes, which are needed to ready the electrodes for DNA base differentiation; however, nanoscale surface mobility represents a major concern for these materials. The extraordinary high surface mobility of gold make it less attractive than palladium for maintaining a fixed-gap width. Though palladium fairs a bit better in this respect, it has been recently discovered that a 3 nm gap cut in palladium nanowires results in retraction or widening of the gap by 0.7 to 2.5 nm after 1 day in air, rendering the gap size too large for the purposes of DNA sequencing. This stability issue is a major problem from a manufacturing perspective as well, wherein commercialization may not be possible due to yield and instability issues. The present application provides a method and structure that address the above stability issue.

Referring first to FIG. 1, there is illustrated a first exemplary structure including, from bottom to top, a semiconductor substrate 10 and a dielectric membrane 12 in accordance with an embodiment of the present application. The dielectric membrane 12 is formed as a contiguous dielectric layer on a front-side surface of the semiconductor substrate 10. Throughout the present application, the term "front-side surface of the semiconductor substrate" denotes a surface of the semiconductor substrate 10 in which there is present an interface with the dielectric membrane 12. Throughout the present application, the term "back-side surface of the semiconductor substrate" denotes a surface of the semiconductor substrate 10 that opposes the surface containing the interface with the dielectric membrane 12.

The semiconductor substrate 10 that can be used in the present application can be a bulk semiconductor substrate. The term "bulk" denotes that the entirety of the semiconductor substrate 10 is comprised of a semiconductor material. Examples of semiconductor materials that can be employed as the semiconductor substrate include, but not limited to, Si, Ge, SiGe, SiC, SiGeC, and III/V compound semiconductors such as, for example, InAs, GaAs, and InP. Multilayers of these semiconductor materials can also be used as the semiconductor material of the bulk semiconductor. In one embodiment, the semiconductor substrate 10 can be comprised of a single crystalline semiconductor material, such as, for example, single crystalline silicon. In other embodiments, the semiconductor substrate 10 may comprise a polycrystalline or amorphous semiconductor material. In yet other embodiments, semiconductor substrate 10 may comprise a multilayered stack of semiconductor materials that are in epitaxial alignment with each other.

The semiconductor substrate 10 may have any crystal orientation including, for example, {100}, {110}, or {111}. Other crystallographic orientations besides those specifically mentioned can also be used in the present application for the semiconductor substrate 10.

The semiconductor substrate 10 that is employed in the present application may be an intrinsic semiconductor material. By "intrinsic" it is meant that the semiconductor substrate 10 has a dopant concentration of less than $1\times10^{15}$ atoms/cm$^3$. In other embodiments, the semiconductor substrate 10 may contain a p-type dopant or an n-type dopant. The dopant may be uniformly distributed throughout the entirety of the semiconductor substrate 10 or the dopant may be present as a gradient.

The dielectric membrane 12 that is present on the front-side surface of the semiconductor substrate 10 may be comprised of a semiconductor oxide, a semiconductor nitride and/or a semiconductor oxynitride. In one embodiment of the present application, the dielectric membrane 12 may be comprised of silicon dioxide. In another embodiment of the present application, the dielectric membrane 12 can be comprised of silicon nitride.

In one embodiment of the present application, the dielectric membrane 12 can be formed on the front-side surface of the semiconductor substrate 10 utilizing a deposition such as, for example, chemical vapor deposition, plasma enhanced chemical vapor deposition, or evaporation. In another embodiment of the present application, the dielectric membrane 12 can be formed by a thermal growth process such as, for example, thermal oxidation and/or thermal nitridation. The dielectric membrane 12 that is formed at this point of the present application is a contiguous layer.

In one embodiment of the present application, the dielectric membrane 12 that is formed may have a thickness from 5 nm to 200 nm. Other thicknesses that are lesser than or greater than the aforementioned thickness range can also be used for the dielectric membrane 12 of the present application.

Figure 2:
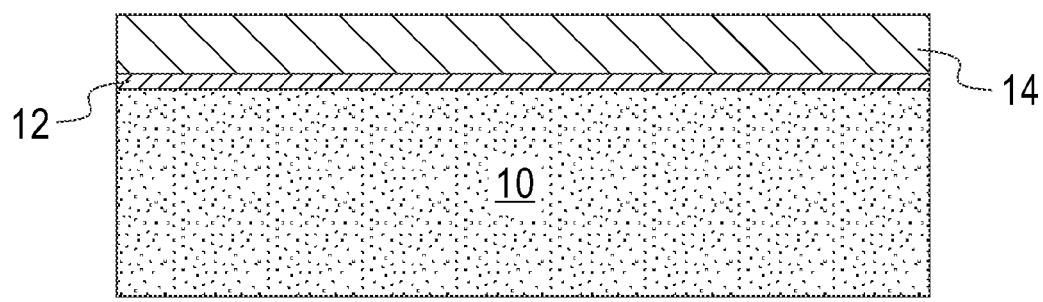
FIG. 2 is a cross sectional view of the first exemplary structure of FIG. 1 after forming a protective layer on the dielectric membrane.

Referring now to FIG. 2, there is illustrated the first exemplary structure of FIG. 1 after forming a protective layer 14 on the dielectric membrane 12. The protective layer 14 that can be used in the present application comprises a different material than that of the dielectric membrane 12. Moreover, the protective layer 14 that is employed in the present application includes any material such as, for example, a dielectric material and/or a diffusion barrier material, which can prevent any damage to the dielectric membrane 12 during subsequently performed processing steps that are performed on the back-side surface of the semiconductor substrate 10. Additionally, the protective layer 14 should also have high etch selectivity compared with the dielectric membrane 12 so that it can be removed when back-side processing is complete without any thinning of the dielectric membrane 12.

In one embodiment, the protective layer 14 may comprise an oxide, such as, for example, silicon dioxide. In other embodiment, the protective layer 14 may include a multilayered stack of, from bottom to top, an oxide and a metal nitride. For example, the protective layer 14 may include a multilayered stack of, from bottom to top, silicon dioxide and TiN.

The protective layer 14 can be formed on an exposed upper surface of the dielectric membrane 12 utilizing well known deposition processes. For example, a chemical vapor deposition process utilizing tetraethylorthosilate (TEOS) or other silicon dioxide forming gases can be used. When a metal nitride is used as a portion of the protective layer 14, the metal nitride can be formed utilizing a deposition process such as, for example, chemical vapor deposition, plasma enhanced chemical vapor deposition, physical vapor deposition or chemical solution deposition.

In one embodiment of the present application, the protective layer 14 that is formed may have a thickness from 500 nm to 700 nm. Other thicknesses that are lesser than or greater than the aforementioned thickness range can also be used for the protective layer 14 of the present application.

Figure 3:
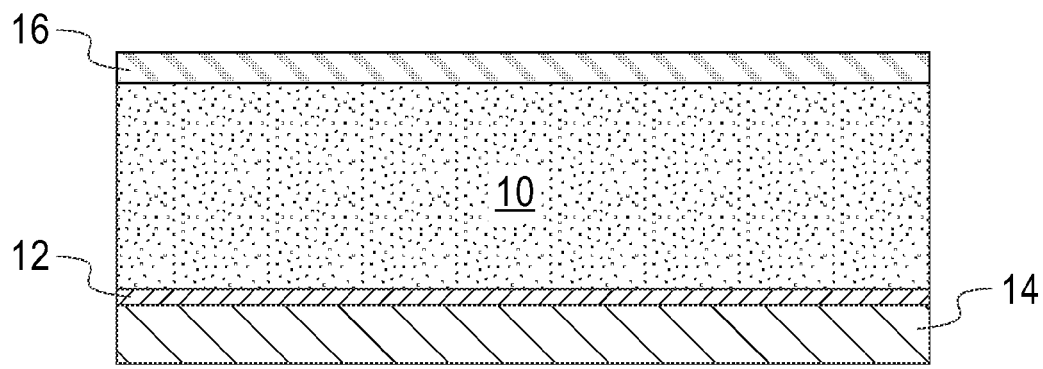
FIG. 3 is a cross sectional view of the first exemplary structure of FIG. 2 after rotating the structure 180° and forming a hard mask on a surface of the semiconductor substrate opposite the surface containing the dielectric membrane.

Referring now to FIG. 3, there is illustrated the first exemplary structure of FIG. 2 after rotating the structure 180° and forming a hard mask 16 on a surface (i.e., back-side surface) of the semiconductor substrate 10 opposite the surface containing the dielectric membrane 12. The hard mask 16 is a contiguous layer that covers an entirety of the back-side surface of the semiconductor substrate 10 that is opposite the surface of the semiconductor substrate 10 including dielectric membrane 12. The rotating of the structure shown in FIG. 2 by 180° may be performed by hand or by any mechanical means including, for example, a robot arm.

The hard mask 16 that can be employed in this embodiment of the present application may include a dielectric oxide, a dielectric nitride, a dielectric oxynitride or any multilayered combination thereof. In some embodiments, the hard mask 16 may comprise a different dielectric material than the dielectric membrane 12. In other embodiments, the hard mask 16 may comprise a same dielectric material as the dielectric membrane 12. In one embodiment, the hard mask 16 is a dielectric oxide such as silicon dioxide, while in another embodiment the hard mask 16 is a dielectric nitride such as silicon nitride.

The hard mask 16 can be formed utilizing a deposition process including, for example, chemical vapor deposition (CVD), plasma enhanced chemical vapor deposition (PECVD), chemical solution deposition, evaporation, or physical vapor deposition (PVD). Alternatively, the hard mask 16 may be formed by one of thermal oxidation, and thermal nitridation. The thickness of the hard mask 16 employed in the present application may vary depending on the material of the hard mask 16 itself as well as the technique used in forming the same. Typically, and in one embodiment, the hard mask 16 has a thickness from 100 nm to 300 nm. Other thicknesses that are greater than or lesser than the aforementioned thickness range can also be used for the thickness of the hard mask 16.

Figure 4:
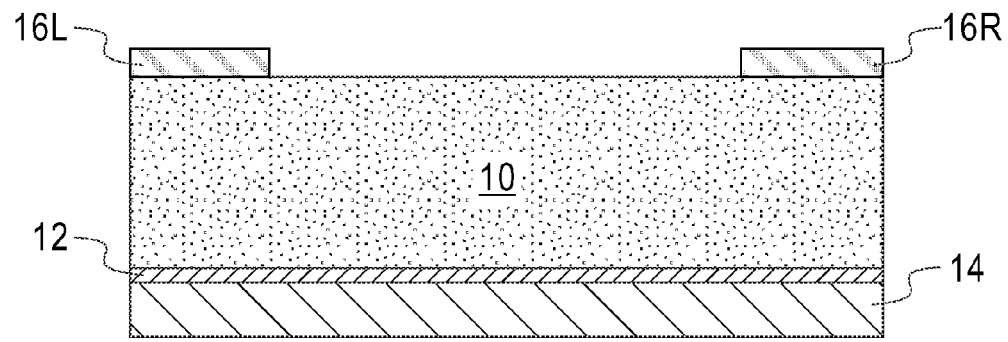
FIG. 4 is a cross sectional view of the first exemplary structure of FIG. 3 after patterning the hard mask.

Referring now to FIG. 4, there is illustrated the first exemplary structure of FIG. 3 after patterning the hard mask 16.

The remaining portions of the hard mask 16 that are formed after patterning may be referred to herein as a first hard mask portion 16L and a second hard mask portion 16R. The first hard mask portion 16L and the second hard mask portion 16R that are provided can be used in a subsequent processing step as an etch mask.

Patterning of the hard mask 16 can be performed by lithography and etching. Lithography can include forming a photoresist (not shown) on the topmost surface of the hard mask 16, exposing the photoresist to a desired pattern, and then developing the exposed photoresist with a conventional resist developer to provide a patterned photoresist atop the hard mask 16. An etch is then employed which transfers the pattern from the patterned photoresist into the hard mask 16. In one embodiment, the etch used for pattern transfer may include a dry etch process such as, for example, reactive ion etching, plasma etching, ion beam etching or laser ablation. In another embodiment, the etch used for pattern transfer may include chemical etching process. In one example, tetramethylammonium hydroxide (TMAH) can be used as the chemical etchant. After transferring the pattern into hard mask 16, the patterned photoresist can be removed utilizing a resist stripping process such as, for example, ashing.

Figure 5:
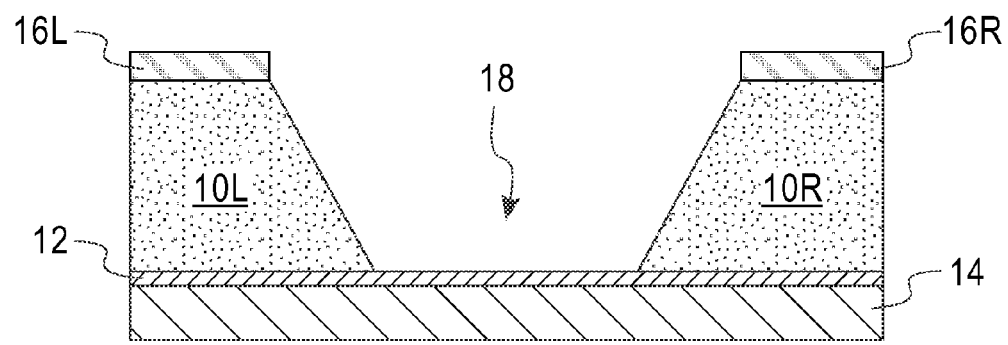
FIG. 5 is a cross sectional view of the first exemplary structure of FIG. 4 after providing an opening within the semiconductor substrate using remaining portions of the hard mask as an etch mask.

Referring now to FIG. 5, there is illustrated the first exemplary structure of FIG. 4 after providing an opening 18 within the semiconductor substrate 10 using the remaining portions of the hard mask 16L, 16R as an etch mask. The opening 18 is formed inward from the back-side surface of semiconductor substrate 10 to the front-side surface of the semiconductor substrate 10. The remaining portions of the semiconductor substrate 10 may be referred to herein as a first semiconductor material portion 10L and a second semiconductor material portion 10R. The opening 18 that is provided exposes a surface of the dielectric membrane 12 that is opposite the surface of the dielectric membrane 12 that includes the protective layer 14. Although the drawings, and following description, illustrate the presence of a single opening 18, a plurality of openings can be formed inward from the back-side surface of semiconductor substrate 10.

In some embodiments, the opening 18 that is formed into the semiconductor substrate 10 may have sidewalls that are perpendicularly oriented to the bottom surface of the dielectric membrane 12. In other embodiments, the opening 18 that is formed into the semiconductor substrate 10 has tapered sidewalls. In some cases, the tapering of the sidewalls of the opening 18 may expand outwards from the bottom surface of the dielectric membrane 12 to the back-side surface of the semiconductor substrate 10 such that a width of the opening 18 that is nearest to the bottommost surface of the dielectric membrane 12 is less than a width of the opening 18 that is nearest to the back-side surface of the semiconductor substrate 10. In some cases, the tapering of the sidewalls of the opening may contract outwards from the bottom surface of the dielectric membrane 12 to the back-side surface of the semiconductor substrate 10 such that a width of the opening 18 the is nearest to the bottommost surface of the dielectric membrane 12 is greater than a width of the opening 18 that is nearest to the back-side surface of the semiconductor substrate 10. Notwithstanding the type of opening 18 formed, the opening 18 has a width that is greater than a width of a nanogap to be subsequently formed in the dielectric membrane 12.

The opening 18 that is formed into the semiconductor substrate 10 can be provided utilizing an etching process that is selective for removing semiconductor material as compared to remaining hard mask portions 16L, 16R and dielectric membrane 12. The etch process may be an isotropic etch or an anisotropic etch. In some embodiments, a crystallographic etch can be used in providing the opening 18. By "crystallographic etch" it is meant an etching process, typically a wet etch, in which etching occurs preferentially along selected crystallographic planes in a crystalline solid. In one example and when silicon is used as the semiconductor substrate 10, the opening 18 can be formed utilizing tetramethylammonium hydroxide (TMAH).

Figure 6:
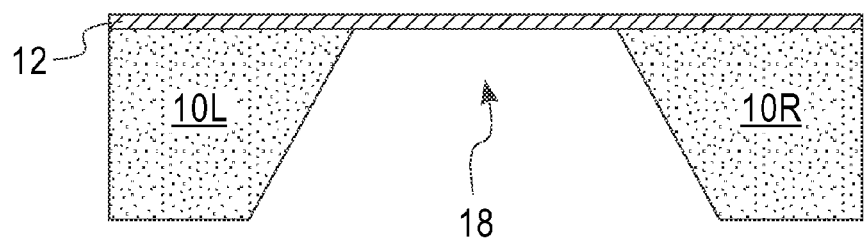
FIG. 6 is a cross sectional view of the first exemplary structure of FIG. 5 after removing the remaining portions of the hard mask, rotating the structure 180° and removing the protective layer.

Referring now to FIG. 6, there is illustrated the first exemplary structure of FIG. 5 after removing the remaining portions of the hard mask 16L, 16R, rotating the structure 180° and removing the protective layer 14. In some embodiments of the present application, the removal of the remaining portions of the hard mask 16L, 16R can be omitted and the remaining portions of the hard mask 16L, 16R can be left within the final nanodevice of the present application. The removal of the protective layer 14 from the structure exposes the upper surface of the dielectric membrane 12.

In embodiments in which the remaining portions of the hard mask 16L, 16R are removed, an etching process can be used to remove the remaining portions of the hard mask 16L, 16R from the structure. The rotating of the structure can be performed by hand or any mechanical means including, for example, a robot arm. The protective layer 14 can be removed by a planarization process such as, for example, chemical mechanical planarization and/or grinding. Alternatively, an etching process can be used to remove the protective layer 14.

Figure 7:
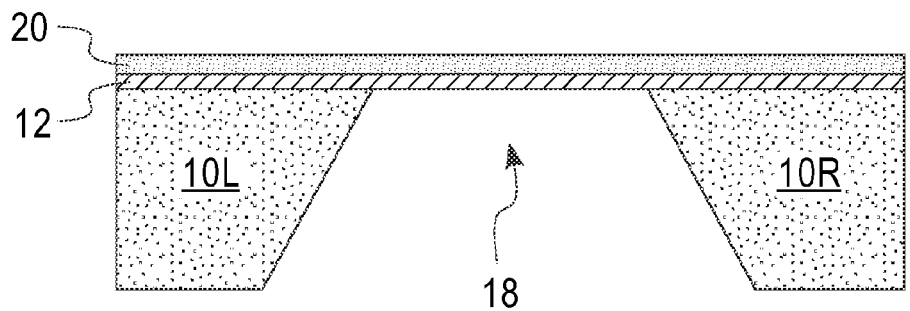
FIG. 7 is a cross sectional view of the first exemplary structure of FIG. 6 after forming a nanowire.

Referring now to FIG. 7, there is illustrated the first exemplary structure of FIG. 6 after forming a nanowire 20 on the exposed surface of the dielectric membrane 12. It is noted that the nanowire 20 does not necessary span the entire length of the underlying dielectric membrane 12. It is also noted that although a single nanowire 20 is described and illustrated, a plurality of nanowires 20 can be formed.

The nanowire 20 may include at least one transition metal from Group VIB, VIII and IB of the Periodic Table of Elements. In one embodiment, the nanowire 20 is selected from the group consisting of palladium, platinum and/or gold. The nanowire 20 may include a single layered structure or it may include a multilayered structure including at least two different metals stack one on top of the other.

The nanowire 20 can be formed be first forming a layer of nanowire material (not specifically shown) on an exposed surface of the dielectric membrane 12 utilizing a deposition process including, for example, chemical vapor deposition, plasma chemical vapor deposition, atomic layer deposition, physical vapor deposition, sputtering, or plating. After deposition the layer of nanowire material, the nanowire 20 can be formed by patterning the layer of nanowire material. In one embodiment of the present application, the patterning of the layer of nanowire material may include e-beam lithography and a lift-off technique. In another embodiment of the present application, the patterning of the layer of nanowire material may include lithography and etching.

In one embodiment of the present application, the nanowire 20 that is formed may have a height from 2 nm to 20 nm. Other heights that are lesser than or greater than the aforementioned range can also be used for the nanowire 20 of the present application. The nanowire 20 can have a length from 20 nm to 1000 nm. The width of nanowire 20, as measured from one sidewall surface of the nanowire 20 to an opposing sidewall surface of the nanowire 20, can be from 2 nm to 50 nm.

Figure 8:
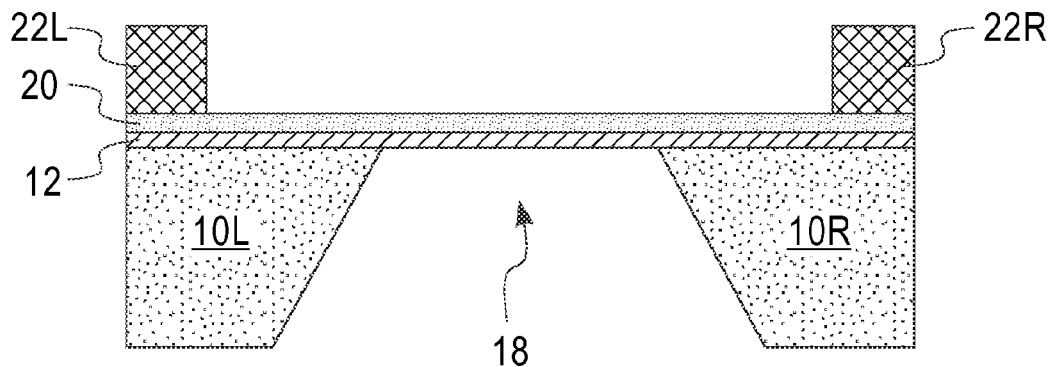
FIG. 8 is a cross sectional view of the first exemplary structure of FIG. 7 after forming metal pads on portions of the nanowire.

Referring now to FIG. 8, there is illustrated the first exemplary structure of FIG. 7 after forming metal pads 22L, 22R on portions of the nanowire 20. In one embodiment, the metal pads 22L, 22R can be comprised of a same metal or metal alloy as the nanowire 20. In another embodiment, the metal pads 22L, 22R can be comprised of a different metal or metal alloy as nanowire 20. Notwithstanding which embodiment is employed, the metal pads 22L, 22R can include at least one transition metal from Group VIB, VIII and IB of the Periodic Table of Elements. In one embodiment, each metal pad 22L, 22R is selected from the group consisting of palladium, platinum and/or gold.

The metal pads 22L, 22R that are formed have a thickness that is generally greater than the thickness of the nanowire 20. The metal pads 22L, 22R can be formed utilizing the same techniques as mentioned above in forming the nanowire 20. That is, the metal pads 22L, 22R can be formed by depositing a blanket layer of a metal pad material. The blanket layer of metal pad material is then patterned. In one embodiment of the present application, the patterning of the blanket layer of metal pad material may include e-beam lithography and a lift-off technique. In another embodiment of the present application, the patterning of the blanket layer of metal pad material may include lithography and etching.

Figure 9:
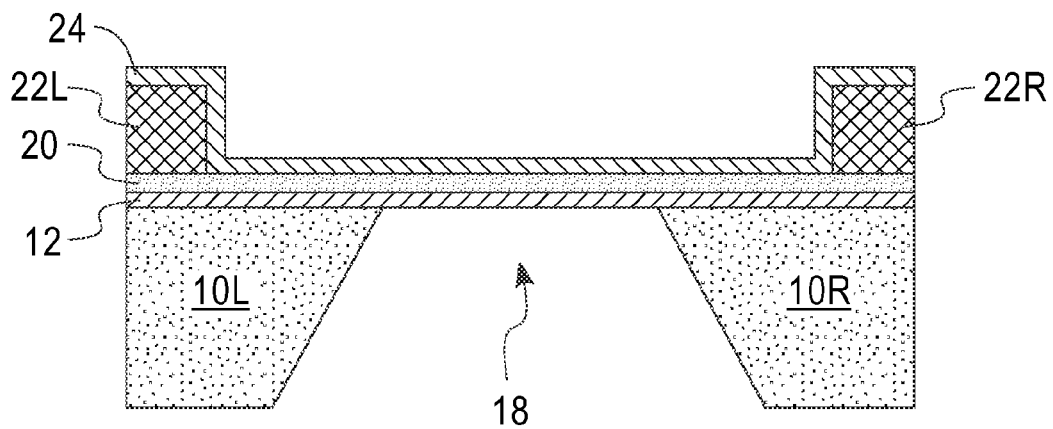
FIG. 9 is a cross sectional view of the first exemplary structure of FIG. 8 after coating the nanowire and metal pads with an anti-retraction capping material.

Referring now to FIG. 9, there is illustrated the first exemplary structure of FIG. 8 after coating the nanowire 20 and the metal pad 22L, 22R with an anti-retraction capping material 24. The anti-retraction capping material 24 is a contiguous layer that is formed on exposed surfaces (sidewalls and upper surface) of the nanowire 20 and exposed surfaces (sidewalls and upper surface) of each metal pad 22L, 22R. The anti-retraction capping material 24 is used in the present application to prevent the retraction of subsequently formed nanowire portions of the nanodevice of the present application during their use. The anti-retraction capping material 24 can also act as a mobility barrier to pin the nanowire portions (to be subsequently formed) in place, allowing long-term stability.

The anti-retraction capping material 24 that is used in the present application has an adequate compressive stress and shares some covalent bonds with the nanowire 20 beneath it. By "adequate compressive stress" it is meant that a sufficient compressive stress is present to counteract the natural tendency of the nanowire material retract after a gap 26 has been formed. Covalent bonds between the nanowire 20 and anti-retraction capping material 24 are necessary for the capping material 24 to hold the cut nanowires 20L, 20R, to be subsequently formed in place. In some embodiments, the anti-retraction capping material 24 may be a dielectric material. In other embodiments, the anti-retraction capping material 24 may be composed of a non-electrically insulating material.

In one embodiment of the present application, aluminum oxide can be used as the anti-retraction capping material 24. In another embodiment of the present application, titanium nitride can be used as the anti-retraction capping material 24. In a further embodiment, silicon nitride can be used as the anti-retraction capping material 24. Other materials which can prevent diffusion of conductive atoms from the nanowire 20 can be used as the anti-retraction capping material. The anti-retraction capping material 24 may be a single layered structure, or it can be a multilayered structure including at least two different anti-retraction capping materials stacked one atop of the other. Hence, anti-retraction capping material 24 may include a stack of, from bottom to top, a layer of silicon nitride and a layer of titanium nitride. In embodiments in which hard mask portions 16L, 16R are retained on the back-side surface of the semiconductor substrate 10, the anti-retraction capping material 24 comprises a different material than that of the hard mask portions 16L, 16R.

The anti-retraction capping material 24 can be formed by a deposition process such as, for example, sputtering or atomic layer deposition. In one embodiment of the present application, the anti-retraction capping material 24 that is formed may have a thickness from 3 nm to 15 nm. Other thicknesses that are lesser than or greater than the aforementioned thickness range can also be used for the anti-retraction capping material 24 of the present application.

Figure 10:
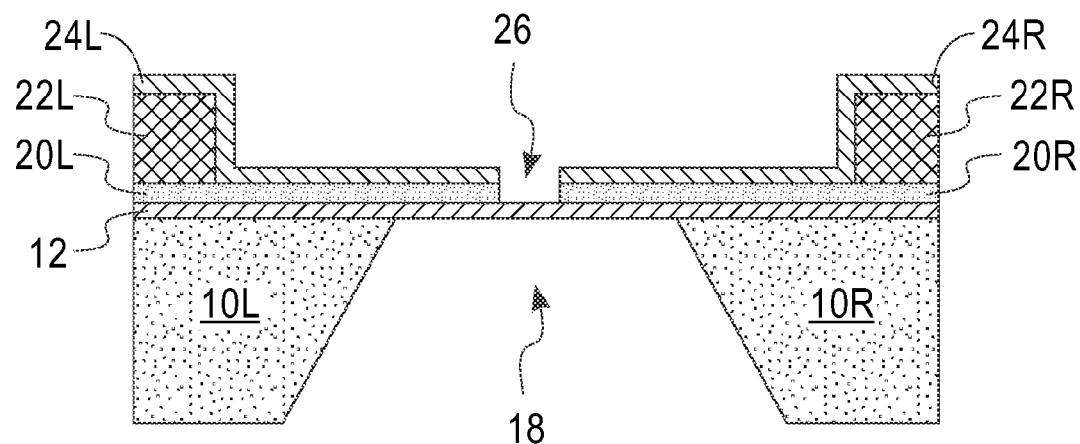
FIG. 10 is a cross sectional view of the first exemplary structure of FIG. 9 after cutting the anti-retraction capping material and the nanowire to provide a first capped nanowire structure and a second capped nanowire structure, wherein the first capped nanowire structure and the second capped nanowire structure are separated by a nanogap of less than 3 nanometers.

Referring now to FIG. 10, there is illustrated the first exemplary structure of FIG. 9 after cutting the anti-retraction capping material 24 and the nanowire 20 to provide a first capped nanowire structure and a second capped nanowire structure, wherein the first capped nanowire structure and the second capped nanowire structure are separated by a nanogap 26 of less than 3 nanometers. In one example, the nanogap 26 between the first capped nanowire structure and the second capped nanowire structure is from 0.2 nm to 2 nm. The nanogap 26 of the present application is formed through both the anti-retraction capping material 24 and the nanowire 20.

In accordance with the present application, the first capped nanowire structure includes a first nanowire portion 20L and a first anti-retraction capping material portion 24L, and the second capped nanowire structure includes a second nanowire portion 20R and a second anti-retraction capping material portion 24R. The first and second nanowire portions 20L, 20R are used as the electrodes of the nanodevice of the present application.

The first capped nanowire structure (20L, 24L) and the second capped nanowire structure (20R, 24R) can be formed by cutting the anti-retraction capping material 24 and the nanowire 20.

In one embodiment of the present application, the cutting of the anti-retraction capping material 24 and the nanowire 20 may include a helium ion beam cutting process in which a helium ion microscope can be used. In such a cutting process, helium ions are irradiated from the helium ion microscope and are used in the present application in forming the nanogap 26. Any conventional helium ion microscope including, for example, ORION™ Helium Ion Microscope from Carl Zeiss SMT or the Multiple Ion Beam Microscopes from Carl Zeiss SMT can be used in the present application.

Some exemplary helium ion microscope conditions that can be used for cutting the anti-retraction capping material 24 and the nanowire 20 and thus forming nanogap 26 are now described. Notably, and in some embodiments, a voltage from 10 kilovolts to 30 kilovolts, a beam current of from 25 pA (picoamperes) to 1500 pA, a beam spot size of from 3.4 Å to 5 Å, a step size of from 5 Å to 50 Å, a working distance of from 5 millimeters to 10 millimeters, an aperture opening from 7.5 micrometers to 30 micrometers, and a exposure time from 0.5 µs/pixel to 2.0 µs/pixel can be used in the present application in providing the nanogap 26 through both the anti-retraction capping material 24 and the nanowire 20.

In another embodiment of the present application, the cutting of the anti-retraction capping material 24 and the nanowire 20 may include the use of a focused transmission electron microscope (TEM) beam cutting process. When such a process is used, any conventional focused transmission electron microscope (TEM) beam cutting apparatus can be used. The conditions that can be used when a focused transmission electron microscope (TEM) beam cutting apparatus is employed in forming the nanogap 26 vary and can be optimized to provide a nanogap having a dimension of 3 nm or less.

In yet a further embodiment, the cutting of the anti-retraction capping material 24 and the nanowire 20 may include the use of a combination of a helium ion beam cutting and focused transmission electron microscope (TEM) beam cutting.

Figure 11:
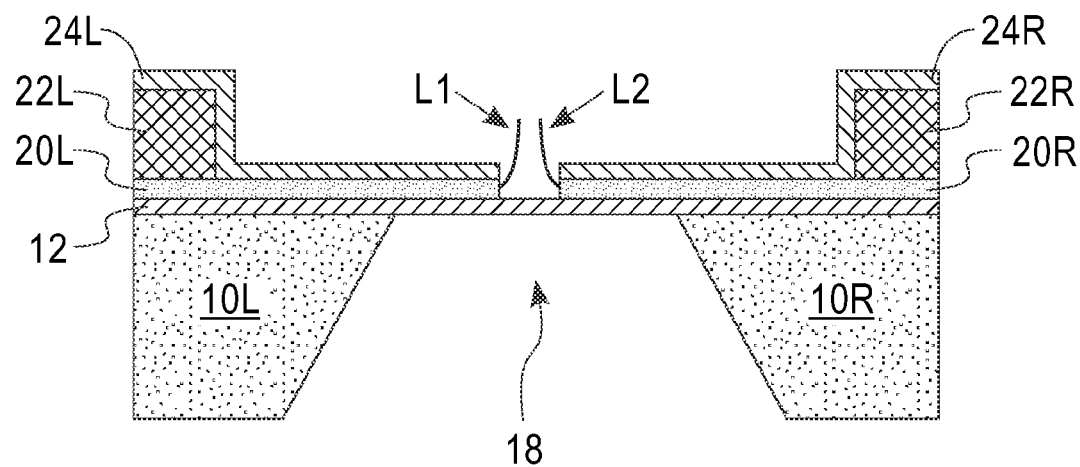
FIG. 11 is a cross sectional view of the first exemplary structure of FIG. 10 after forming a first linker molecule on an exposed edge of a first nanowire portion of the first capped nanowire structure and a second linker molecule on an exposed edge of a second nanowire portion of the second capped nanowire structure.

Referring now to FIG. 11, there is illustrated the first exemplary structure of FIG. 10 after forming a first linker molecule L1 on an exposed edge of the first nanowire portion 20L of the first capped nanowire structure and a second linker molecule L2 on an exposed edge of the second nanowire portion 20R of the second capped nanowire structure.

The term "linker molecule" as used in the present application denotes a thiolated chemical compound. The first and second linker molecules L1, L2 that can be employed in the present application include, for example, imidazole or benzamide. The first and second linker molecules L1, L2 can be provided to the exposed edge of the first nanowire portion 20L of the first capped nanowire structure and the exposed edge of the second nanowire portion 20R of the second capped nanowire structure by covalent binding.

FIGS. 10 and 11 illustrate a nanogap device in accordance with the present application. The nanogap device includes a dielectric membrane 12 located on a front-side surface of a semiconductor substrate 10L, 10R. A first capped nanowire structure (20L and 24L) is located on a first portion of the dielectric membrane 12, and a second capped nanowire structure (20R and 24R) is located on a second portion of the dielectric membrane. In accordance with the present application, the first capped nanowire structure (20L and 24L) and the second capped nanowire structure 20R and 24R) are separated by a nanogap 26 of less than 3 nanometers.

Figure 12:
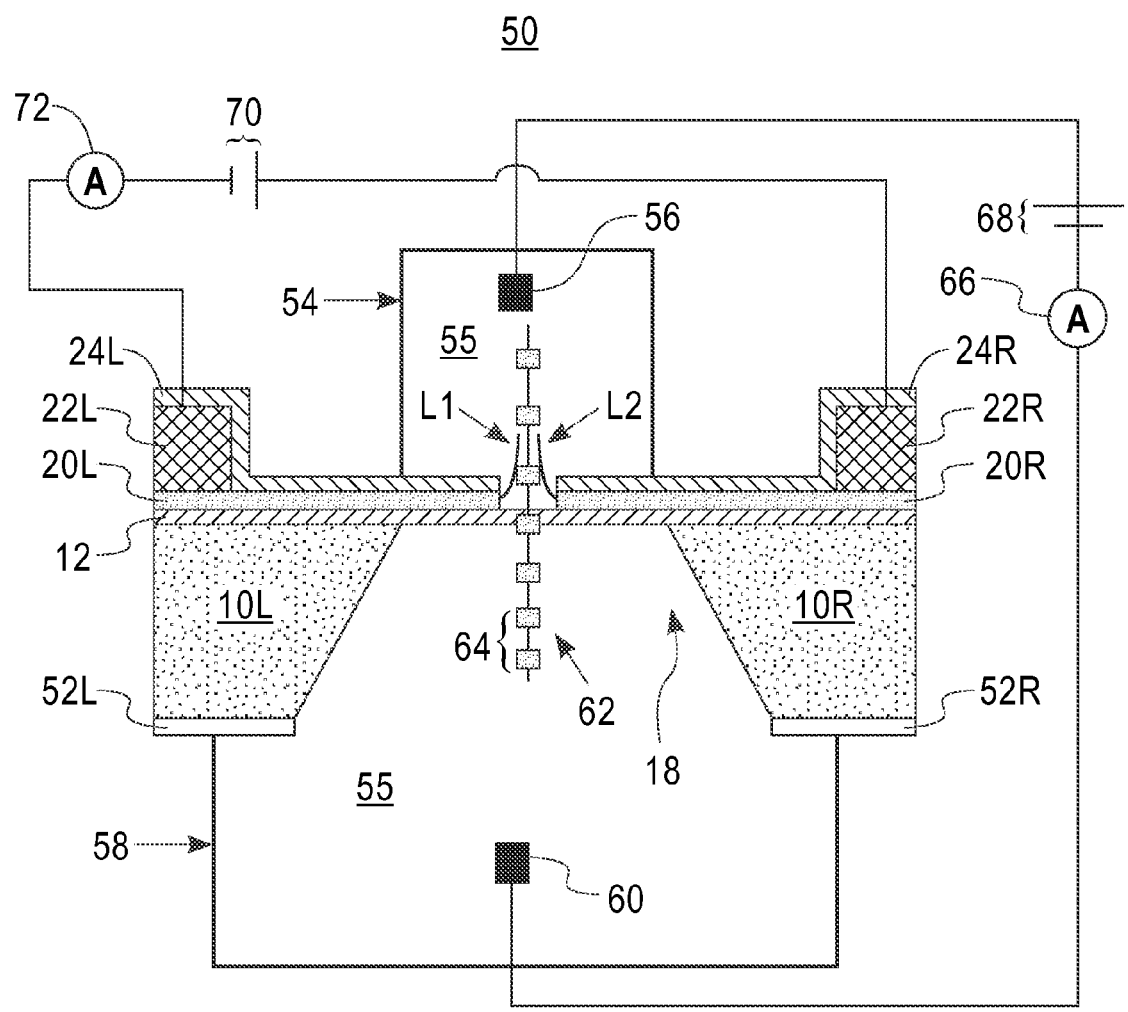
FIG. 12 illustrates a sequencing system utilizing the nanodevice according to an embodiment of the present application.

Referring now to FIG. 12, there is illustrated a system 50 for sequencing using the nanodevice illustrated in FIG. 11. As mentioned above, the nanodevice includes a dielectric membrane 12 located on a front-side surface of a semiconductor substrate 10L, 10R. A first capped nanowire structure (20L and 24L) is located on a first portion of the dielectric membrane 12, and a second capped nanowire structure (20R and 24R) is located on a second portion of the dielectric membrane. In accordance with the present application, the first capped nanowire structure (20L and 24L) and the second capped nanowire structure 20R and 24R) are separated by a nanogap 26 of less than 3 nanometers. A backside cavity provided by opening 18 between semiconductor material portions 10L,10R forms a suspended membrane making up the nanogap.

In the system 50, a top reservoir 54 is attached and sealed to the top of each anti-retraction capping material portion 24L, 24R, and a bottom reservoir 58 is attached and sealed to the bottom of each insulating film portions 52L, 52R. The insulating film portions 52L, 52R include one of the materials mentioned above for the hard mask. An electrode 56 is present in the top reservoir 54, and another electrode 60 is present in the bottom reservoir 58. Electrodes 56, 60 may be silver/silver chloride, or platinum for example. The reservoirs 54 and 58 are the inlet and outlet respectively for buffer solution 55, and reservoirs 54 and 58 hold the DNA and/or RNA samples for sequencing. The buffer solution 55 is an electrically conductive solution (such as an electrolyte) and may be a salt solution such as NaCl.

The system 50 shows a target molecule 62, which is the molecule being analyzed and/or sequenced. As an example DNA sample, the system 50 may include a single stranded DNA molecule as target molecule 62, which is passing through the nanogap and the dielectric membrane 12. The DNA molecule has bases 64 (A, G, C, and T) represented as blocks. The DNA molecule is pulled through the nanogap and dielectric membrane 12 by a vertical electrical field generated by the voltage source 68. When voltage is applied to electrodes 56 and 60 by the voltage source 68, the voltage generates the electric field (between reservoirs 54 and 558) that controllably (e.g., by turning on and off the voltage source 68)

drives the DNA molecule into and through the nanogap and dielectric membrane 12. Also, the voltage of the voltage source 68 can produce the gate bias between metal pads 22L, 22R. Note that the metal pads 22L, 22R and the nanowire portions 20L, 20R, and the nanogap may operate as a transistor. The voltage across the nanogap from the voltage source 68 can be the gate for controlling the transistor. Metal pads (electrodes) 22L, 22R are the drain and source respectively for the transistor device. Voltage applied by voltage source 70 to metal pads 22L, 22R also builds the electrical field, which can hold the base 64 in the nanogap for sequencing. Note that metal pads 22L, 22R are electrically connected to nanowire portions 22L and 22R having the nanogap 26.

Ammeter 66 monitors the ionic current change when DNA (or RNA) molecule (i.e., target molecule 62) goes through nanogap and the dielectric membrane. The ionic current (measured by the ammeter 66) flows through electrode 56, into the buffer solution 56, through the nanogap and the dielectric membrane 12, out through the electrode 60. Voltage generated by the voltage source 70 produces the voltage between the metal pads 22L, 22R. Another ammeter 72 monitors the source-drain transistor current from nanogap to detect nucleotide (i.e., base) information when the DNA/RNA molecule passes through the nanogap and dielectric membrane. For example, when a base 64 is in the nanogap and dielectric membrane 12 and when voltage is applied by the voltage source 70, source-drain transistor current flows to metal pad 24R, into nanowire portion 20R, into the buffer solution 55 to interact with the base 530 positioned therein, into nanowire portion 20L, out through the metal pad 24L, and to the ammeter 72. The ammeter 720 is configured to measure the change in source-drain current when each type of base 64 is present in the nanogap and also when no base 64 is present. The respective bases 64 of the target molecule 62 are determined by the amplitude of the source-drain transistor current when each respective base in present in the nanogap and dielectric membrane 12.

In the following example, a study was performed to show that a capped nanowire structure of the present application exhibited significantly less retraction as compared to a nanowire structure in which the anti-retraction capped material was absent. Notably, a 5 nm thick aluminum oxide anti-retraction capping material was formed by atomic layer deposition on exposed surfaces of a 35 nm-wide palladium nanowire and them TEM cutting was performed in accordance with an embodiment of the present application.

Another palladium nanowire was also cut using TEM however this palladium nanowire did not include any anti-retraction layer thereon. The nanogap sizes of these two devices, i.e., capped nanowire and uncapped nanowire, were measured periodically over 48 hours.

Figure 13:
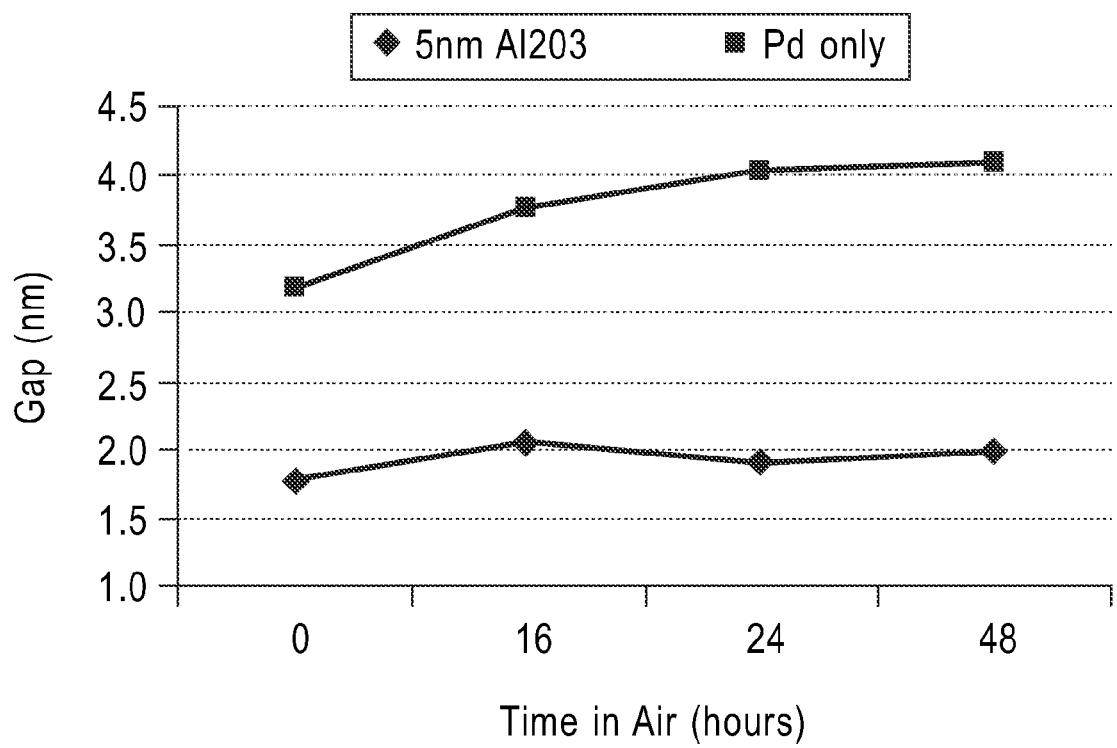
FIG. 13 is a plot of nanogap size (nm) vs. time in air (hours) for a nanodevice including a capped nanowire structure (in accordance with the present application) and for a nanodevice including a non-capped nanowire structure (not in accordance with the present application).

The results are shown in FIG. 13. Notably, the results provided in FIG. 13 show angstrom level change in the minimum dimension of the capped nanowire (i.e., at the resolution level of the TEM), while the non-capped palladium nanowire shows a 0.8 nm increase in the nanogap over the same time period. This result demonstrates the usefulness of providing nanodevices which contain anti-retraction capped nanowires for creating a fixed gap for recognition tunneling.

While the present application has been particularly shown and described with respect to various embodiments thereof, it will be understood by those skilled in the art that the foregoing and other changes in forms and details may be made without departing from the spirit and scope of the present application. It is therefore intended that the present application not be limited to the exact forms and details described and illustrated, but fall within the scope of the appended claims.

What is claimed is:

1. A nanogap device comprising:
a dielectric membrane on a front-side surface of a semiconductor substrate;
a first capped nanowire structure located on a first portion of said dielectric membrane; and
a second capped nanowire structure located on a second portion of said dielectric membrane, wherein said first capped nanowire structure and said second capped nanowire structure are separated by a nanogap of less than 3 nanometers, the nanogap being formed through a nanowire but not through the dielectric membrane;
wherein said first capped nanowire structure includes a first nanowire portion, a first metal pad directly on top of said first nanowire portion, and a first anti-retraction capping material portion directly on top of said first metal pad;
wherein said second capped nanowire structure includes a second nanowire portion, a second metal pad directly on top of said second nanowire portion, and a second anti-retraction capping material portion directly on top of said second metal pad;
wherein said first nanowire portion and said second nanowire portion comprise a same metal, said same metal selected from the group consisting of palladium and platinum.

2. The nanogap device of claim 1, wherein said semiconductor substrate includes an opening located at a back-side surface thereof, said opening exposes a surface of said dielectric membrane that is opposite a surface including said first capped nanowire structure and said second capped nanowire structure.

3. The nanogap device of claim 2, wherein said opening is tapered and has a width that is greater than that of said nanogap.

4. The nanogap device of claim 1, wherein said first capped nanowire structure and said second capped nanowire structure are positioned directly on top of one side of said dielectric membrane in which an opposite side of said dielectric membrane is positioned directly on top of said semiconductor substrate.

5. The nanogap device of claim 4, wherein said first anti-retraction capping material portion and said second anti-retraction capping material portion comprise a same anti-retraction capping material.

6. The nanogap device of claim 5, wherein said anti-retraction capping material is selected from the group consisting of aluminum oxide, titanium nitride and silicon nitride.

7. The nanogap device of claim 4, wherein an exposed edge of said first nanowire portion faces an exposed edge of said second nanowire portion.

8. The nanogap device of claim 7, wherein a first linker molecule is located on said exposed edge of said first nanowire portion and a second linker molecule is located on said exposed edge of said second nanowire portion.

9. The nanogap device of claim 1, wherein said semiconductor substrate comprises silicon.

10. The nanogap device of claim 1, wherein the nanowire is a single nanowire having a height of 2 nanometers.

* * * * *